(12) United States Patent
Vortman et al.

(10) Patent No.: US 10,589,129 B2
(45) Date of Patent: Mar. 17, 2020

(54) THERAPEUTIC ULTRASOUND WITH REDUCED INTERFERENCE FROM MICROBUBBLES

(71) Applicants: Kobi Vortman, Haifa (IL); Shuki Vitek, Haifa (IL); Eyal Zadicario, Tel Aviv-Jaffa (IL); Yoav Levy, Hinanit (IL)

(72) Inventors: Kobi Vortman, Haifa (IL); Shuki Vitek, Haifa (IL); Eyal Zadicario, Tel Aviv-Jaffa (IL); Yoav Levy, Hinanit (IL)

(73) Assignee: INSIGHTEC, LTD., Tirat Carmel (IL)

( * ) Notice: Subject to any disclaimer, the term of this patent is extended or adjusted under 35 U.S.C. 154(b) by 566 days.

(21) Appl. No.: 15/265,204

(22) Filed: Sep. 14, 2016

(65) Prior Publication Data
US 2018/0071553 A1    Mar. 15, 2018

(51) Int. Cl.
| A61N 7/00 | (2006.01) |
| A61N 7/02 | (2006.01) |
| A61B 5/055 | (2006.01) |
| A61B 34/10 | (2016.01) |
| A61B 17/22 | (2006.01) |
| A61B 8/08 | (2006.01) |
| A61B 90/00 | (2016.01) |

(52) U.S. Cl.
CPC .............. *A61N 7/00* (2013.01); *A61N 7/022* (2013.01); *A61B 5/055* (2013.01); *A61B 8/0808* (2013.01); *A61B 8/5223* (2013.01); *A61B 2017/22009* (2013.01); *A61B 2034/104* (2016.02); *A61B 2034/105* (2016.02); *A61B 2090/062* (2016.02); *A61B 2090/067* (2016.02); *A61N 2007/003* (2013.01); *A61N 2007/0021* (2013.01); *A61N 2007/0039* (2013.01); *A61N 2007/0043* (2013.01); *A61N 2007/0052* (2013.01); *A61N 2007/0078* (2013.01); *A61N 2007/0086* (2013.01); *A61N 2007/0091* (2013.01); *A61N 2007/0095* (2013.01)

(58) Field of Classification Search
None
See application file for complete search history.

(56) References Cited

U.S. PATENT DOCUMENTS

| 2007/0016039 A1* | 1/2007 | Vortman | A61B 8/467 600/439 |
| 2008/0319356 A1* | 12/2008 | Cain | A61B 17/22004 601/2 |
| 2013/0046229 A1* | 2/2013 | Konofagou | A61B 17/225 604/22 |
| 2014/0114216 A1* | 4/2014 | Konofagou | A61B 8/481 601/2 |
| 2016/0184616 A1* | 6/2016 | Cain | A61N 7/00 601/2 |
| 2016/0279449 A1* | 9/2016 | Powers | A61B 17/22004 |

* cited by examiner

*Primary Examiner* — Joel F Brutus
(74) *Attorney, Agent, or Firm* — Morgan, Lewis & Bockius LLP

(57) ABSTRACT

Various approaches for reducing microbubble interference with ultrasound waves transmitted from multiple transducer elements and traversing tissue onto a target region include measuring microbubbles in high-throughput areas of ultrasound exposure and reducing the amount of microbubbles using the ultrasound waves.

35 Claims, 8 Drawing Sheets

THERAPEUTIC ULTRASOUND WITH REDUCED INTERFERENCE FROM MICROBUBBLES

FIELD OF THE INVENTION

The field of the invention relates generally to thermal energy treatment systems and, more particularly, to systems and methods for minimizing interferences caused by microbubbles in the thermal energy treatment systems.

BACKGROUND

Focused ultrasound (i.e., acoustic waves having a frequency greater than about 20 kiloHertz) can be used to image or therapeutically treat internal body tissues within a patient. For example, ultrasound waves may be used in applications involving ablation of tumors, thereby eliminating the need for invasive surgery, targeted drug delivery, control of the blood-brain barrier, lysing of clots, and other surgical procedures. During tumor ablation, a piezoceramic transducer is placed externally to the patient, but in close proximity to the tissue to be ablated (i.e., the target). The transducer converts an electronic drive signal into mechanical vibrations, resulting in the emission of acoustic waves. The transducer may be geometrically shaped and positioned along with other such transducers so that the ultrasound energy they emit collectively forms a focused beam at a "focal zone" corresponding to (or within) the target tissue region. Alternatively or additionally, a single transducer may be formed of a plurality of individually driven transducer elements whose phases can each be controlled independently. Such a "phased-array" transducer facilitates steering the focal zone to different locations by adjusting the relative phases among the transducers. As used herein, the term "element" means either an individual transducer in an array or an independently drivable portion of a single transducer. Magnetic resonance imaging (MRI) may be used to visualize the patient and target, and thereby to guide the ultrasound beam.

The noninvasive nature of ultrasound surgery is particularly appealing for the treatment of brain tumors. Moreover, coherent, non-invasive focusing of ultrasound through the human skull has been considered as a tool for targeted drug delivery to the brain, improved thrombolytic stroke treatment, blood flow imaging, the detection of internal bleeding, and tomographic brain imaging. However, the human skull has been a barrier to the clinical realization of ultrasound therapy. Impediments to transcranial ultrasound procedures include strong attenuation and the distortions caused by irregularities in the skull's shape, density, and sound speed, which contribute toward destroying the focus and/or decreasing the ability to spatially register received diagnostic information.

In addition, during a focused ultrasound procedure, small gas bubbles (or "microbubbles") may be generated in the liquid contained in the brain tissue, e.g., due to the stress resulting from negative pressure produced by the propagating ultrasonic waves and/or from when the heated liquid ruptures and is filled with gas/vapor. The reaction of tissue containing a higher relative percentage of microbubbles during the continued application of the ultrasound energy is non-linear and difficult to predict. For example, microbubbles may reflect and/or scatter ultrasound waves, and further deteriorate the focus or reduce the intensity thereof. Additionally, the microbubbles may collapse due to the applied stress from an acoustic field; this mechanism, called "cavitation," may cause extensive tissue damage beyond that targeted, and may be difficult to control. Finally, because microbubbles are typically generated and/or spread in the patient's body in a non-uniform manner, microbubbles accumulating in the skull may further increase the challenge of accounting for the ultrasound distortions resulting from both the skull and microbubbles when estimating/calculating focusing properties.

Accordingly, there is a need to minimize microbubble interference with therapeutic ultrasound waves in order to optimize focusing properties and maximize the amount of acoustic energy available at the focus.

SUMMARY

The present invention provides systems and methods for minimizing microbubble interference with ultrasound waves when the ultrasound waves traverse intervening tissue (e.g., a skull) by "cleaning" microbubbles from a high-throughput area (HTA) of the traversed tissue. In various embodiments, multiple regions within the traversed tissue are defined, with each region corresponding to a transducer element (or a grouping of transducer elements). A predictive model and/or measurements may be utilized to determine characteristics of each region; based thereon and together with a known or expected angle of incidence of the acoustic waves with respect to the traversed tissue, an acoustic energy contributed by each transducer element (or each grouping of transducer elements) after traversing its corresponding region to reach a focal zone can be estimated. Based on the estimated energy contribution, each traversed region may be characterized as an HTA (where the contribution of energy is above a threshold) or a low-throughput area (LTA) (where the contribution of energy is below the threshold).

In one embodiment, microbubbles generated or accumulated in the HTA regions are monitored during a focused ultrasound procedure. If the amount of microbubbles (expressed as an absolute number or as a concentration per unit volume) is above a pre-determined threshold, a microbubble-reducing process is initiated to reduce microbubbles in the HTAs. For example, the microbubbles may be swept from an HTA region into an LTA region using an acoustic radiation force created by the ultrasound waves themselves. Alternatively, an ultrasound steering beam may be created to apply stress on the microbubbles in order to induce microbubble collapse and/or sweep microbubbles from an HTA region into an LTA region. After the number of microbubbles is reduced in the HTA regions, the focused ultrasound procedure may continue (e.g., target treatment may be resumed).

In one implementation, the ultrasound transducer is coupled to a controller including all necessary hardware components and/or software modules to automatically monitor the microbubbles, analyze the amount of microbubbles accumulated in the HTA region(s), performing the microbubble-reducing process and/or start or continue the focused ultrasound procedure. Accordingly, the current invention automatically minimizes microbubble interference with the ultrasound waves in the traversed tissue to thereby maximize an acoustic energy available at the focus; in addition, the current invention advantageously avoids unexpected tissue damages resulting from microbubble cavitation.

Accordingly, in one aspect, the invention provides a method for reducing microbubble interference with ultrasound waves transmitted from multiple transducer elements and traversing a patient's skull into a target region in accordance with a treatment plan. In various embodiments, the method includes (a) identifying high-throughput areas of the skull through which, during execution of the treatment plan, ultrasound energy above a first threshold amount is not expected to pass; (b) monitoring the high-throughput areas for microbubbles during execution of the treatment plan; and (c) if an amount of microbubbles in the high-throughput areas exceeds a threshold, reducing the amount of microbubbles using the ultrasound waves. Each one of the high-throughput areas may correspond to one of the transducer elements or one grouping of the transducer elements.

In various embodiments, the method includes generating a focus (e.g., a point focus or a line focus) having an acoustic radiation force is first generated and using the acoustic radiation force to sweep the microbubbles outside the high-throughput areas. For example, the acoustic radiation force may sweep the microbubbles from the high-throughput areas to low-throughput areas of the skull; ultrasound energy above a second threshold amount (which is typically smaller than the first threshold amount) is not expected to pass through the low-throughput areas during execution of the treatment plan. In some embodiments, particularly if there are no low-throughput areas adjacent to a high-throughput area, the acoustic radiation force sweeps the microbubbles from the high-throughput areas to intermediate-throughput areas of the skull; ultrasound energy above the first threshold amount is not expected to pass through the intermediate-throughput areas but ultrasound energy above the second threshold amount is expected to pass therethrough.

In some embodiments, the method includes generating an ultrasound steering beam and using the steering beam to apply stress on the microbubbles to induce collapse thereof. The ultrasound steering beam may be generated by physically moving the transducer elements with respect to the microbubbles or by adjusting relative phases of the transducer element.

The high-throughput areas may be identified based at least in part on a physical model, a measurement of transmitted or reflected ultrasound waves, images acquired using an imaging device, and/or an angle of incidence of the ultrasound waves with respect to the patient's skull. The angle of incidence may be computed based at least in part on geometry of the transducer elements and their locations and orientations relative to the skull and a location of the target region. In addition, the microbubbles may be monitored based at least in part on ultrasound waves reflected therefrom and/or analysis of images acquired by an imaging device. The amount of microbubbles may be defined as an absolute number thereof or as a concentration per unit volume.

In another aspect, the invention is directed to an ultrasound treatment system including an ultrasound transducer having multiple transducer elements and a controller. In various embodiments, the controller is configured to (a) operate the transducer in accordance with a treatment plan to focus ultrasound waves onto tissue within a patient's skull; (b) identify, based at least on the treatment plan and an orientation of the transducer with respect to the skull, high-throughput areas of the skull through which, during execution of the treatment plan, ultrasound energy above a first threshold amount is expected to pass; (c) monitor the high-throughput areas for microbubbles during execution of the treatment plan; and (d) if an amount of microbubbles in the high-throughput areas exceeds a threshold, reduce the amount of microbubbles using the ultrasound waves. In some embodiments, the system further includes a detector device, coupled to the controller, for measuring the amount of the microbubbles. Additionally, the system may include an imager, coupled to the controller, for measuring the amount of the microbubbles.

The controller may be further configured to operate the transducer to generate a focus (e.g., a point focus or a line focus) having an acoustic radiation force and to use the acoustic radiation force to sweep the microbubbles outside the high-throughput areas. For example, the acoustic radiation force may sweep the microbubbles from the high-throughput areas to low-throughput areas of the skull; ultrasound energy above a second threshold amount, which is typically smaller than the first threshold amount, is not expected to pass through the low-throughput areas during execution of the treatment plan. In some embodiments, the acoustic radiation force sweeps the microbubbles from the high-throughput areas to intermediate-throughput areas of the skull; ultrasound energy above the first threshold amount is not expected to pass through the intermediate-throughput areas but ultrasound energy above the second threshold amount is expected to pass therethrough.

In some embodiments, the controller is further configured to generate an ultrasound steering beam to apply stress on the microbubbles and thereby induce collapse thereof. The controller is configured to physically move the transducer elements with respect to the microbubbles so as to generate the ultrasound steering beam. Alternatively, the controller is configured to adjust relative phases of the transducer elements so as to generate the ultrasound steering beam.

In addition, the controller may be configured to identify the high-throughput areas based at least in part on a physical model. Alternatively, the system may include a detector device, coupled to the controller, for measuring the focus ultrasound waves or ultrasound waves reflected from the patient's skull, with the controller configured to identify the high-throughput areas based on the measurement of the detector device. In one embodiment, the system includes an imager, coupled to the controller, for acquiring images, and the controller is configured to identify the high-throughput areas based on the images. In another embodiment, the controller is further configured to compute an angle of incidence of the ultrasound waves with respect to the patient's skull based at least in part on geometry of the transducer elements and their locations and orientations relative to the patient's skull and a location of the tissue. In addition, the controller may be configured to define the amount of microbubbles as an absolute number thereof or as a concentration per unit volume.

As used herein, the term "substantially" means ±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1:
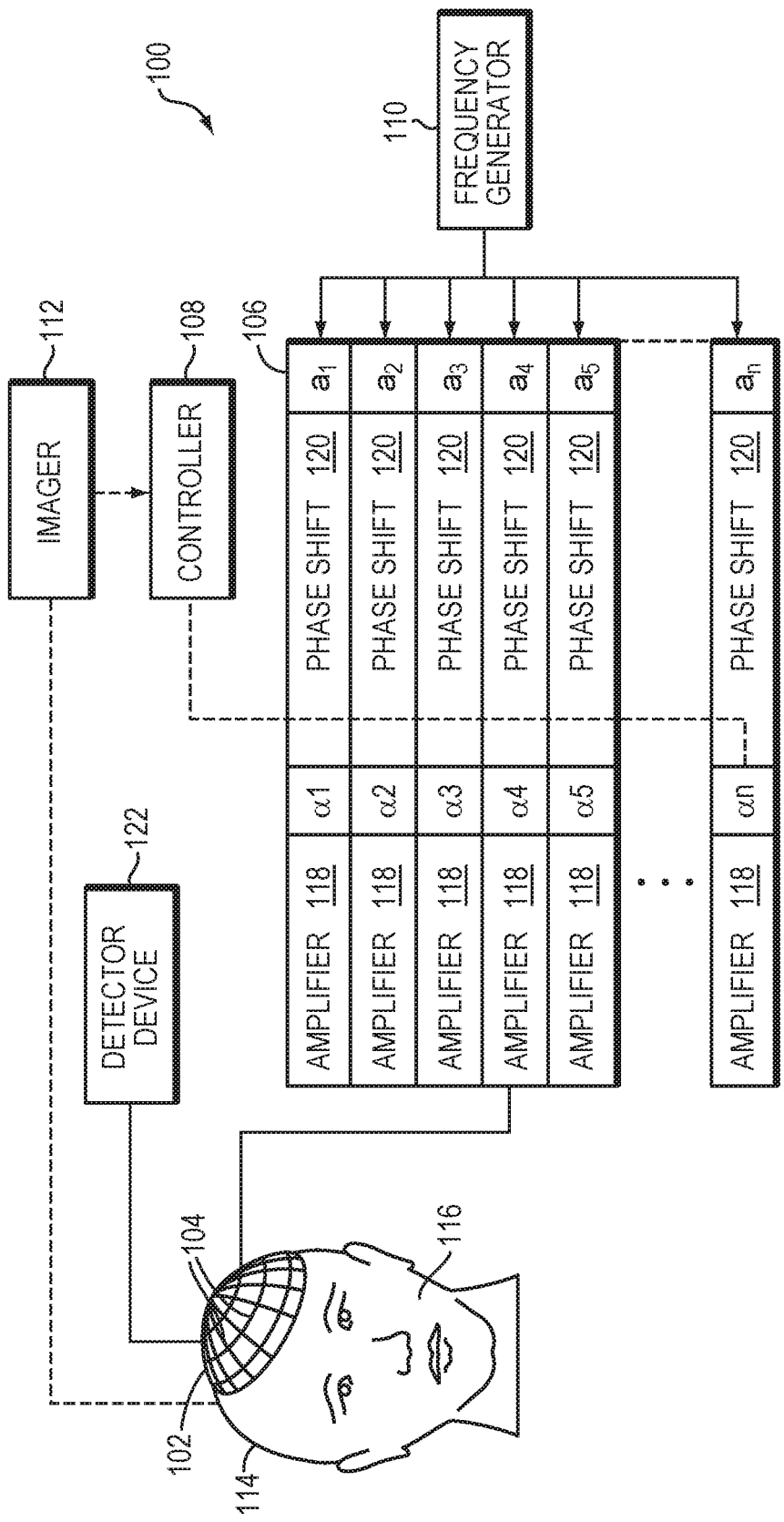
FIG. 1 illustrates a focused ultrasound system in accordance with various embodiments.

FIG. 1 illustrates an exemplary ultrasound therapy system 100 for focusing ultrasound within a patient's brain through the skull. One of ordinary skill in the art, however, will understand that the ultrasound system 100 described herein may be applied to any part of the human body. In various embodiments, the system 100 includes a phased array 102 of transducer elements 104, a beamformer 106 driving the phased array 102, a controller 108 in communication with the beamformer 106, and a frequency generator 110 providing an input electronic signal to the beamformer 106. In various embodiments, the system further includes an imager 112, such as a magnetic resonance imaging (MRI) device, a computer tomography (CT) device, a positron emission tomography (PET) device, a single-photon emission computed tomography (SPECT) device, or an ultrasonography device, for determining anatomical characteristics of the skull 114 of a patient 116.

The array 102 may have a curved (e.g., spherical or parabolic) shape suitable for placing it on the surface of the skull 114 or a body part other than the skull, or may include one or more planar or otherwise shaped sections. Its dimensions may vary, depending on the application, between millimeters and tens of centimeters. The transducer elements 104 of the array 102 may be piezoelectric ceramic elements, and may be mounted in silicone rubber or any other material suitable for damping the mechanical coupling between the elements 104. Piezo-composite materials, or generally any materials capable of converting electrical energy to acoustic energy, may also be used. To assure maximum power transfer to the transducer elements 104, the elements 104 may be configured for electrical resonance at 50Ω, matching input connector impedance.

The transducer array 102 is coupled to the beamformer 106, which drives the individual transducer elements 104 so that they collectively produce a focused ultrasonic beam or field. For n transducer elements, the beamformer 106 may contain n driver circuits, each including or consisting of an amplifier 118 and a phase delay circuit 120; drive circuit drives one of the transducer elements 104. The beamformer 106 receives a radio frequency (RF) input signal, typically in the range from 0.1 MHz to 1.0 MHz, from the frequency generator 110, which may, for example, be a Model DS345 generator available from Stanford Research Systems. The input signal may be split into n channels for the n amplifiers 118 and delay circuits 120 of the beamformer 106. In some embodiments, the frequency generator 110 is integrated with the beamformer 106. The radio frequency generator 110 and the beamformer 106 are configured to drive the individual transducer elements 104 of the transducer array 102 at the same frequency, but at different phases and/or different amplitudes.

The amplification or attenuation factors $\alpha_1$-$\alpha_n$ and the phase shifts $a_1$-$a_n$ imposed by the beamformer 106 serve to transmit and focus ultrasonic energy through the patient's skull 114 onto a selected region of the patient's brain, and account for wave distortions induced in the skull 114 and soft brain tissue. The amplification factors and phase shifts are computed using the controller 108, which may provide the computational functions through software, hardware, firmware, hardwiring, or any combination thereof. For example, the controller 108 may utilize a general-purpose or special-purpose digital data processor programmed with software in a conventional manner, and without undue experimentation, in order to determine the phase shifts and amplification factors necessary to obtain a desired focus or any other desired spatial field patterns. In certain embodiments, the computation is based on detailed information about the characteristics (e.g., structure, thickness, density, etc.) of the skull 114 and their effects on propagation of acoustic energy. Such information may be obtained from the imager 112 as further described below. Image acquisition may be three-dimensional or, alternatively, the imager 112 may provide a set of two-dimensional images suitable for reconstructing a three-dimensional image of the skull 114 from which thicknesses and densities can be inferred. Image-manipulation functionality may be implemented in the imager 112, in the controller 108, or in a separate device.

System 100 may be modified in various ways within the scope of the invention. For example, for diagnostic applications, the system may further include a detector device 122 that measures transmitted or reflected ultrasound, and which may provide the signals it receives to the controller 108 for further processing. The reflection and transmission signals may also be used as feedback for the phase and amplitude adjustments of the beamformer 106. The system 100 may contain a positioner for arranging the array 102 of transducer elements 104 with respect to the patient's skull 114. In order to apply ultrasound therapy to body parts other than the brain, the transducer array 102 may take a different (e.g., cylindrical) shape. In some embodiments, the transducer elements 104 are mounted movably and rotatably, providing mechanical degrees of freedom that can be exploited to improve focusing properties. Such movable transducers may be adjusted by conventional actuators, which may be driven by a component of controller 108 or by a separate mechanical controller.

Figure 2A:
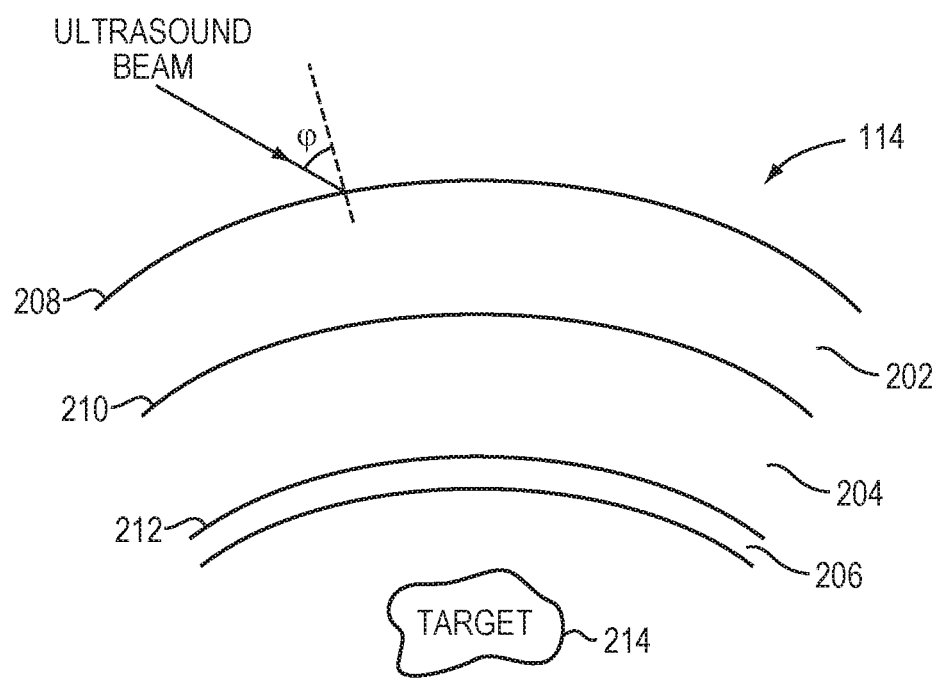
FIG. 2A schematically illustrates tissue layers of a human skull.

Referring to FIG. 2A, a typical human skull 114 has multiple tissue layers, including an external layer 202, a bone marrow layer 204, and an internal layer or cortex 206; each layer of the skull 114 may be highly irregular in shape, thickness and density, and be unique to a patient. As a result, when the ultrasound waves emitted from the system 100 encounter the skull 114, part of the incident acoustic energy may be reflected at the interfaces 208, 210, 212 depending on an angle of incidence, φ, of the waves with respect to the skull 114; the remaining energy may be partially absorbed, and partially refracted and propagated through the skull 114 depending on the frequency of the waves and the structural inhomogeneity of the skull 114. Because the frequency of the ultrasound waves is controllable, the effects of wave propagation through the skull 114 and the focusing properties at the target region 214 may be accurately estimated in accordance with an angle of incidence, $\varphi$, of the acoustic waves with respect to the skull and the structural inhomogeneity of the skull 114 (e.g., thickness, density, and/or shape of each layer 202-206) through which the ultrasound waves emitted from the transducer elements travel prior to reaching the target region 214.

Figure 2B:
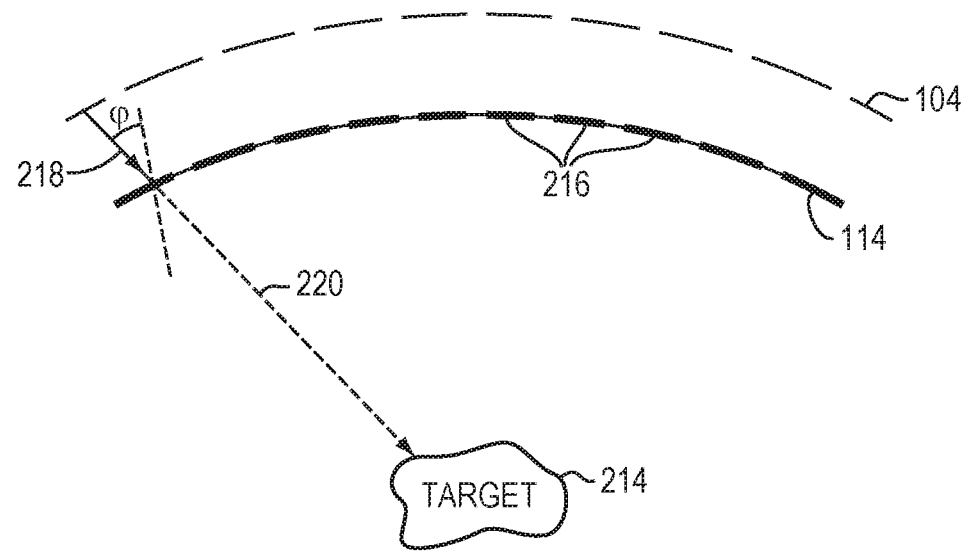
FIG. 2B depicts a skull being defined as multiple regions in accordance with various embodiments.

Referring to FIG. 2B, the skull 114 may be defined as multiple regions 216, each of which may be related to or correspond to a particular transducer element 104 or a grouping of elements. In various embodiments, the angle of incidence, $\varphi$, of the acoustic wave 218 transmitted from each transducer element 104 (or each grouping of elements) onto each skull region 216 can be computed based on information about the geometry of the transducer elements 104 and their locations and orientations relative to the skull regions 216 as well as the location of the target region 214; this information may be obtained using the imager 112 as described above. The angle of incidence, $\varphi$, may be then analyzed using Snell's law to estimate a path 220 of the acoustic waves 218 transmitted from a particular transducer element 104, traversing the skull region 216 and reaching the target region 214 in the brain. This analysis may be repeated for each skull region 216 to acquire a complete set of estimated paths of the acoustic waves traversing the skull regions 216.

In some embodiments, the structural inhomogeneity of the skull region 202 along each estimated path 220 is determined by images acquired using the imager 112. For example, CT imaging may be used to extract the anatomical characteristics of the skull regions 216, such as the skull thickness, local bone densities and/or directional or geometrical features including a normal relative to a surface region of the skull. Methods of creating a local geometric model or mapping of the skull regions 216 are described, for example, in U.S. Patent Publication No. 2010/0179425, the entire disclosure of which is hereby incorporated by reference. In addition, the structural inhomogeneity of each skull region 216 may be characterized using an indicator that can be quantified at the microstructure level of the skull 114; the indicator is determined based on the skull density measured in images acquired using the imager 112. This method is described in U.S. Patent Publication No. 2016/0184026, the entire disclosure of which is hereby incorporated by reference.

Figure 2C:
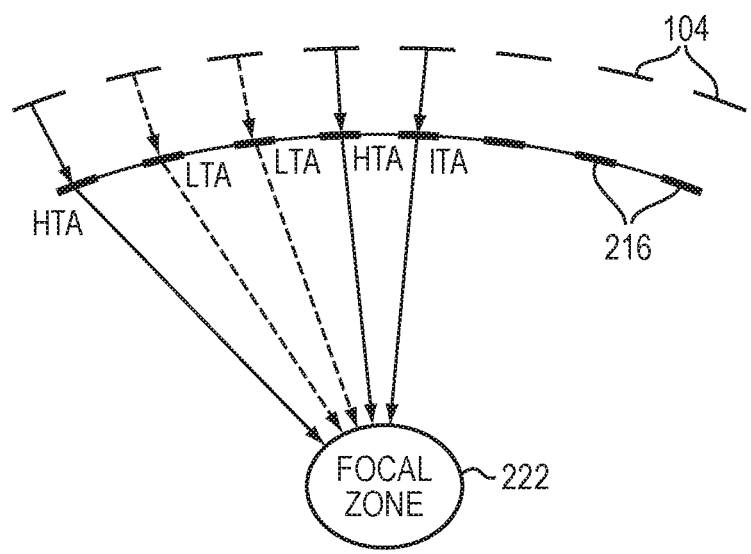
FIGS. 2C and 2D depict characterizing each skull region as a low-throughput area, an intermediate-throughput area or a high-throughput area in accordance with various embodiments.

In various embodiments, information about the angle of incidence of the acoustic waves with respect the skull regions 216, the beam paths 220 of the acoustic waves 218 traversing the skull regions, and the characteristics of each skull region 216 can be used to estimate acoustic energy reflected from the surface of each skull region 216 as well as energy attenuated and/or absorbed within each skull region 216. Based on the estimation, acoustic energy at a focal zone contributed from each transducer element 104 (or each grouping of transducer elements) after traversing its corresponding skull region 216 can be computed. Referring to FIG. 2C, if the energy contribution from a transducer element is below a threshold, the skull region 216 corresponding thereto is characterized as a low-throughput area (LTA); if the contribution from a transducer element is above the threshold, the skull region 216 corresponding thereto is characterized as a high-throughput area (HTA). In some embodiments, the skull region 216 is characterized as an intermediate-throughput area (ITA) if the energy contribution corresponding thereto differs from the threshold by less than a certain percentage (e.g., 10%, 5% or 1%). In this situation, the skull region having a corresponding energy contribution above the percentage plus the threshold is characterized as an HTA, and the skull region having a corresponding energy contribution below the threshold minus the percentage is characterized as an LTA. For example, assuming the threshold is X %, a skull region having an associated energy contribution above (X+5)% is characterized as an HTA, between (X±5)% is characterized as an ITA, and below (X−5)% is characterized as an LTA. Characterization of each skull region (i.e., whether it is an LTA, ITA, or an HTA) may be stored in the system memory and retrieved prior to or during a focused ultrasound procedure to minimize microbubbles generated and/or accumulated in the HTA skull regions.

Figure 2D:
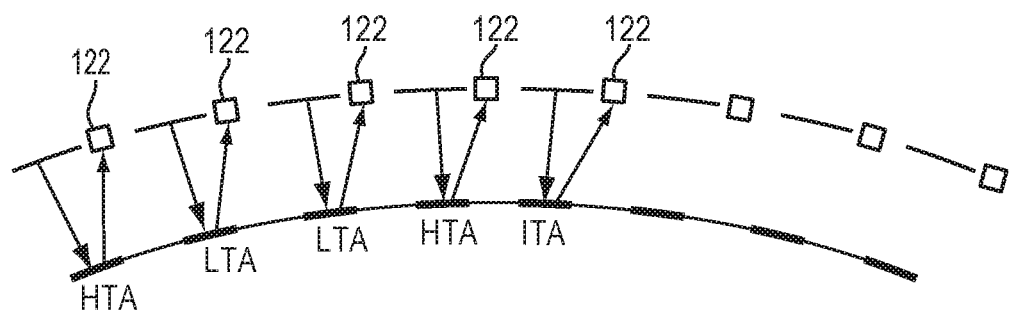

Alternatively, referring to FIG. 2D, characterization of a skull region as an LTA region, ITA region, or an HTA region may be based on transmitted or reflected ultrasound waves measured by the detector device(s) 122 and/or the transducer elements 104. For example, the detector device(s) 122 may measure ultrasound reflections from each skull region 216 and transmit the resulting signals to the controller 108 to obtain information (such as the intensities) associated with the reflections. A threshold (e.g., 50%) may be chosen such that a reflection intensity thereabove indicates that the associated skull region 216 along the beam path is reflective and thus is characterized as an LTA region. Likewise, if the reflection intensity is below the threshold, the skull region 216 along the beam path is characterized as an HTA region. If a percentage (e.g., 5%) deviation from the threshold (e.g., 50%) is utilized to define an ITA region, a skull region having a reflection intensity between 45% and 55% is characterized as an ITA, above 55% is characterized as an LTA, and below 45% is characterized as an HTA.

Figure 3A:
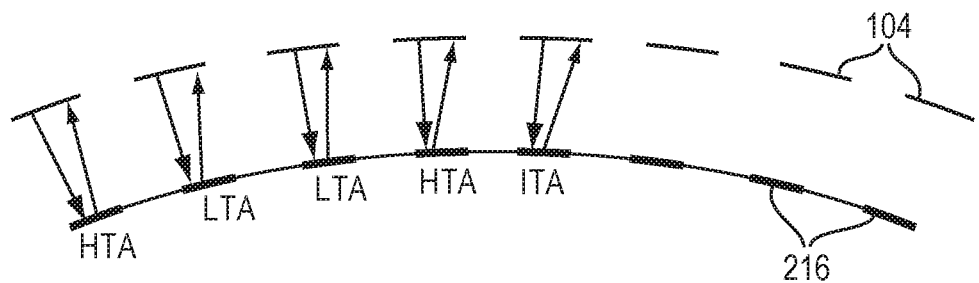
FIGS. 3A-3C depict various configurations of the transducer elements performing a microbubble-reducing procedure in accordance with various embodiments.
Figure 3B:
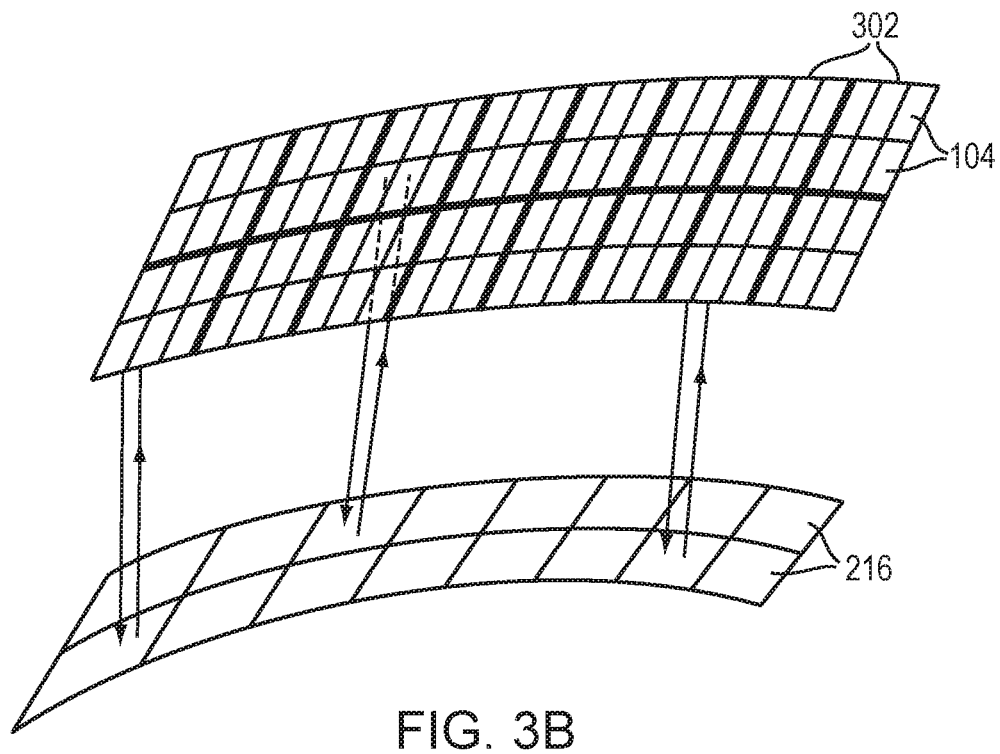
Figure 3C:
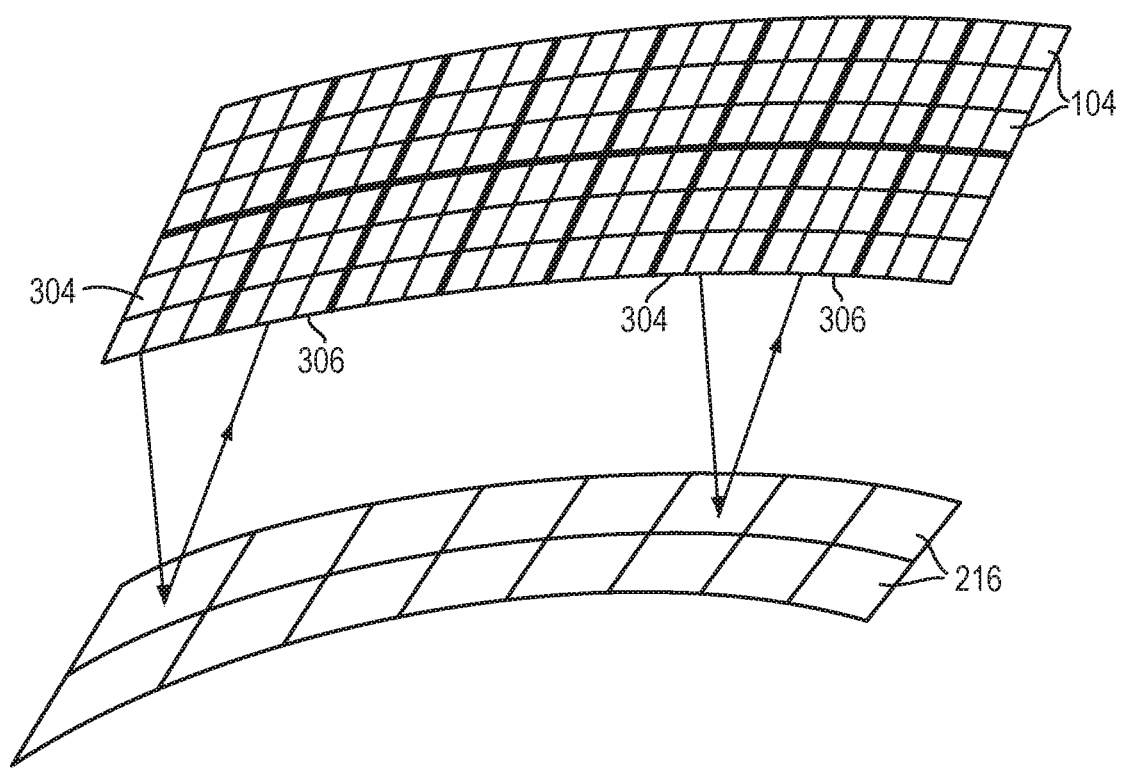

Alternatively, the transducer elements 104 may possess both transmit and detect capabilities. Referring to FIG. 3A, in one embodiment, each individual transducer element 104 alternates between transmitting ultrasound signals to the skull and receiving ultrasound signals reflected therefrom. For example, all transducer elements 104 may substantially simultaneously transmit ultrasound to the skull and subsequently receive echo signals therefrom. Referring to FIG. 3B, in one implementation, the transducer array is divided into multiple sub-regions 302; each sub-region 302 comprises a one- or two-dimensional array (i.e., a row or a matrix) of transducer elements 104. The sub-regions 302 may be separately controllable, i.e., they are each capable of (i) emitting ultrasound waves at amplitudes and/or phases that are independent of the amplitudes and/or phases of the other sub-regions 302, and (ii) measuring reflected waves off the skull. In one embodiment, the sub-regions 302 are assigned different amplitudes and/or phases from one another, and activated, one at a time, to transmit ultrasound to and receive reflections from the skull. Referring to FIG. 3C, in another embodiment, the transducer array is divided into a transmit region 304 and a receive region 306; transducer elements in the transmit region 304 transmit the ultrasound waves while transducer elements in the receive region 306 receive the reflected waves. The received reflected waves are then transmitted to the controller 108 for determining the characterization (e.g., an HTA, an ITA, or an LTA) of the skull regions. The transmit region 304 and receive region 306 of may be configured in different patterns and shapes at various locations of the transducer array. In one implementation, the angle of incidence, φ, is used to determine the association between each receiving region 306 and its corresponding skull area.

During a focused ultrasound procedure (e.g., during treatment of the target region), small gas bubbles (or "microbubbles" having diameters ranging from 0.1 μm to a few hundred μm) may be generated in the tissue, e.g., due to the stress resulting from negative pressure produced by the propagating ultrasonic waves and/or from when the heated liquid ruptures and is filled with gas/vapor. The microbubbles tend to accumulate near interfaces of the skull. The formation and/or amount of microbubbles in the skull regions is monitored using, for example, images acquired by the imager 112. Alternatively, the detector device 122 may detect the microbubbles using reflections therefrom; this is because the microbubbles encapsulate gas and may therefore reflect ultrasound.

Figure 4A:
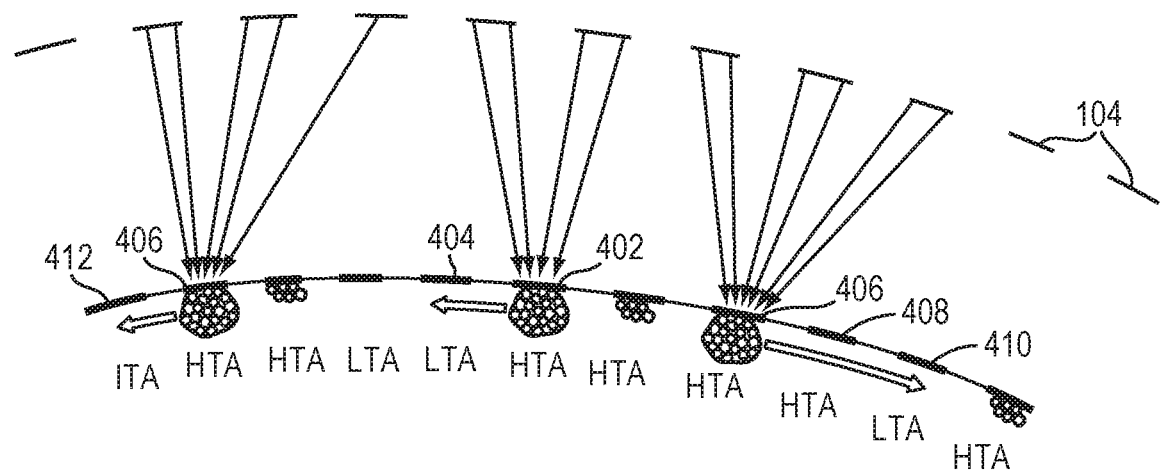
FIG. 4A depicts an approach for sweeping microbubbles from a skull region into another skull region in accordance with various embodiments.

Referring to FIG. 4A, in various embodiments, if the number or concentration of microbubbles in an HTA skull region 402 is above a pre-determined threshold and this HTA region 402 neighbors an LTA region 404, the controller 108 operates the beamformer 106 so as to reduce the bubble population in the region 402. In one embodiment, the controller 108 causes the beamformer 106 to provide drive signals to the transducer elements 104 to generate a focus (e.g., a point focus, a line focus or any suitable shape of focus) at a location including the accumulated microbubbles to sweep enough of them from the HTA region 402 to a neighboring LTA region 404 to reduce the amount of microbubbles below the threshold. Each HTA region may correspond to a different LTA region; more than one HTA region may share the same LTA region. In addition, if an HTA region 406 region does not neighbor any LTA regions, microbubbles accumulated therein may be moved gradually, passing through the intervening HTA(s) 408, before arriving at the closest LTA 410. Alternatively, the controller 108 may cause the transducer elements 104 to generate a focus that sweeps microbubbles from an HTA region 406 to a neighboring ITA region 412 in the absence of an LTA region neighboring the HTA region 406.

It should be understood that the terms "point focus" and "line focus," as used herein, do not refer to points and lines in the strict mathematical sense, but to focus shapes that approximates a point or line, respectively. Thus, the intensity distribution of a point focus (which may, for example, take the shape of a two-dimensional Gaussian distribution) may be characterized by half-widths in both dimensions of the focal plane on the order of a few acoustic wavelengths, whereas the intensity distribution of a line focus (which may, for example, have a one-dimensional Gaussian profile perpendicular to the line) is extended along the direction of the line, but may have a half-width perpendicular thereto on the order of only a few acoustic wavelengths.

In various embodiments, the focus induces the movement of microbubbles by applying an acoustic radiation force thereto. The acoustic radiation force is produced by a change in the density of energy and momentum of the propagating ultrasound waves resulting from absorption, scattering or reflection from the skull. Generally, the amplitude of the acoustic radiation force is proportional to the ultrasound intensity. Accordingly, in one implementation, the intensity of the ultrasound beams directed to the microbubbles gradually increases until the generated acoustic radiation force suffices to manipulate and move the microbubbles. In another embodiment, prior to manipulation of the microbubbles, the characteristics (e.g., an absorption coefficient) of the skull are measured and/or predicted as described above; the intensity of ultrasound beams sufficient for moving the microbubbles can be computed based thereon. In various embodiments, the controller 108 is configured to automatically adjust the ultrasound intensity to start microbubble-reducing processes when the number thereof in the HTA region(s) is above the threshold. Because the energy attenuation resulting from the HTA skull regions is less significant than that resulting from the LTA regions, minimizing microbubbles in the HTA regions may decrease reflections and/or scattering caused by the microbubbles, and thereby increase acoustic energy available at the focal zone 222. In addition, unexpected damage of healthy tissue resulting from microbubble cavitation may be minimized. In some embodiments, the beam intensities emitted from the transducer elements associated with the LTA region(s) and/or ITA region(s) to which microbubbles are swept are reduced as a result; this may avoid undesired ultrasound reflections and/or scattering from the LTA and/or ITA region(s) caused by the microbubbles therein and allow the beam intensities in these regions to be reduced. That is, because the energy contribution at the focus from the LTA and/or ITA regions is relatively small anyway, reducing the beam intensities in these regions may not significantly decrease acoustic energy available at the focal zone 222.

Figure 4B:
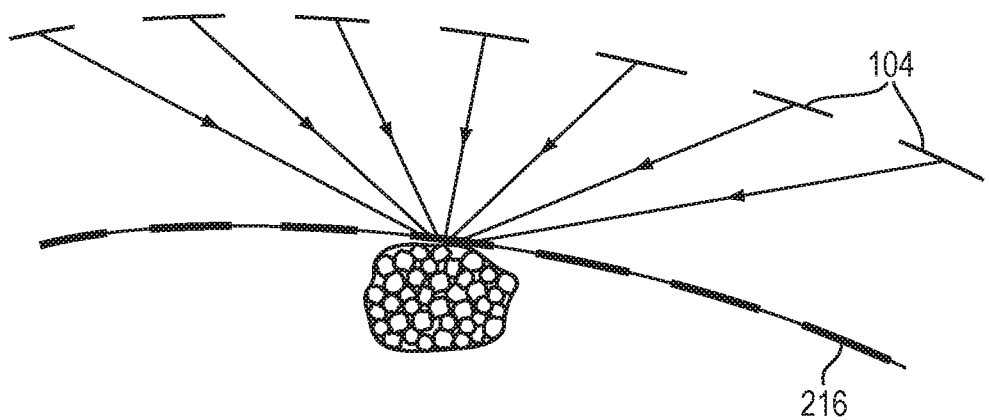
FIG. 4B depicts an approach for inducing microbubble collapse in accordance with various embodiments.

Alternatively, referring to FIG. 4B, when the accumulated amount of microbubbles is above the pre-determined threshold (measured using, for example, reflections from the microbubbles), a steering ultrasound beam is created to apply stress on the microbubbles and thereby induce microbubble collapse. The steering beam may scan across the areas with microbubbles in a discrete or continuous manner until a substantial portion of microbubbles collapse. Generally, the generated microbubbles oscillate at a frequency of the delivered ultrasound waves and have equilibrium radii determined by the resonant frequency thereof:

$$f_0 = \frac{1}{2\pi}\left[\frac{3\kappa P_0}{\rho R_0^2} + \frac{4\sigma}{\rho R_0^3}\right]^{\frac{1}{2}}$$

where $f_0$, $P_0$, and $R_0$ represent the resonant frequency, the ambient pressure, and the equilibrium microbubble radius, respectively, and σ, κ, and ρ represent the surface tension at the liquid-gas interface, the polytropic exponent of the gas, and the density of liquid, respectively. Because the equilibrium radii of the microbubbles are typically a few micrometers, the relationship between the equilibrium radius and resonant frequency can be approximated as:

$$f_0 \sim R_0^{-1}.$$

Accordingly, the equilibrium radius of the microbubbles having at a resonant frequency of 1 MHz is approximately 1 μm, and the equilibrium radius of the microbubbles having at a resonant frequency of 0.5 MHz is approximately 2 μm. Microbubbles having a radius less than one half of the equilibrium radius are likely to be unstable and cause inertial cavitation.

The frequency of the steering beam may be the same as that of ultrasound waves creating microbubbles, or alternatively, it may be reduced in order to increase microbubbles collapse. For example, when the frequency of the steering ultrasound beam is $f_0$, the microbubbles having radii below $R_0/2$ may be induced to collapse. However, by reducing the frequency of the steering ultrasound beam to $f_0/2$, the equilibrium radius of the microbubbles is increased to $2R_0$; this indicates that a larger amount of microbubbles (i.e., microbubbles having radii below $R_0$) may collapse. In some embodiments, the ultrasound steering beam applies sufficient stress on the microbubbles to sweep microbubbles from an HTA region into an LTA region or an ITA region in a manner as described above.

The ultrasound steering beam may be generated mechanically or electrically. In one embodiment, the transducer elements 104 are physically moved with respect to the microbubbles to steer them mechanically. Mechanical steering is particularly suitable when the transducer array is substantially larger than the skull (e.g., about 30 cm or more in diameter) to provide sufficient freedom of movement. In another embodiment, electronic steering resulting from adjustments of relative phase of the acoustic energy emitted by the transducer elements is used. The degree of control provided by such electronic steering is inversely proportional to the size of the individual transducer elements. For example, it is generally desirable to have the size of the transducer elements be on the order of the wavelength of the acoustic energy emitted by the array, and preferably as small as half the wavelength, in order to effectively steer the ultrasound beams. Thus, with acoustic energy having a wavelength on the order of two millimeters (2 mm), as is often used for focused ultrasound systems, transducer elements having a similar size, i.e., about two millimeters or less in cross-section would be needed for effective steering. The electronic steering is preferred as there is no physical movement of the transducer array and such a steering technique is relatively fast.

In various embodiments, the above described microbubble-reducing processes (either by sweeping microbubbles from an HTA region into an LTA region and/or inducing microbubble collapse in the HTA region) can be repeated in the same HTA region until the accumulated microbubbles are below the threshold; again, this may be verified using images acquired by the imager 112 or reflected signals detected by the detector device 112. In addition, the microbubble-reducing processes may be iteratively applied to all (or at least some) HTA skull regions until the accumulated microbubbles therein are minimized. Subsequently, the controller 108 may energize the transducer elements 104 with pre-determined treatment parameters to transmit ultrasound waves to the target region to start or continue treatment. In one embodiment, the treatment parameters (including frequencies, amplitudes, and/or phases of the transducer elements 104 and a sonication time) are pre-determined based on the measured and/or predicted characteristics of the skull as described above in order to generate a focal zone having desired focal properties. In some embodiments, transducer elements corresponding to the LTA skull regions are deactivated and only transducer elements corresponding to the HTA skull regions are activated during treatment; this may advantageously generate sufficient acoustic energy in the focal zone for treatment purposes while avoiding damaging non-target tissue located along the paths of LTA skull regions.

In another embodiment, prior to transmitting the ultrasound to the target region to start or resume the treatment, characteristics of the patient's skull are assessed by measuring ultrasound reflections therefrom or analyzing images acquired by the imager 112; this may increase treatment efficiency and accuracy, in particular when the skull characteristics utilized for determining the HTA regions and LTA regions are acquired based on the model prediction.

Figure 5:
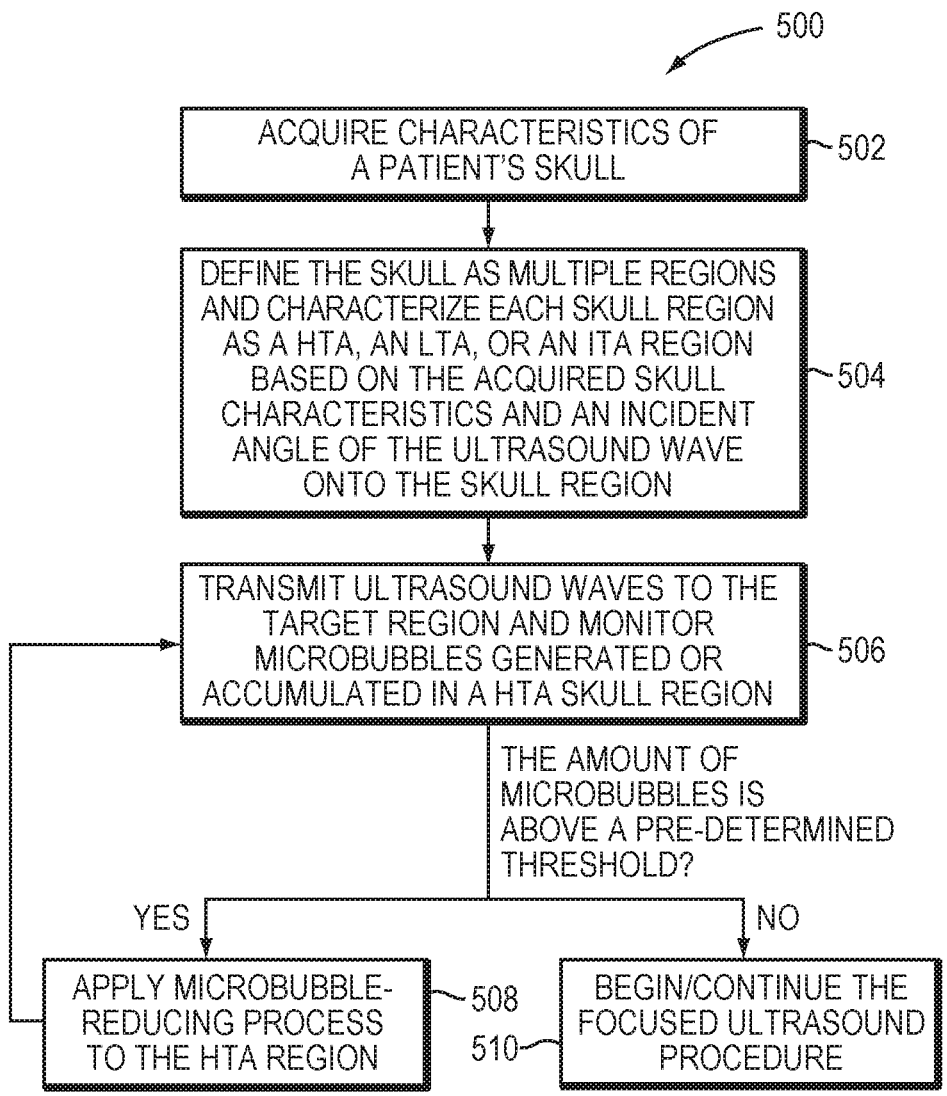
FIG. 5 is a flow chart illustrating an approach for minimizing microbubble interference with ultrasound waves in accordance with various embodiments.

FIG. 5 is a flow chart 500 illustrating an approach for minimizing microbubble interference with ultrasound waves when the ultrasound waves traverse tissue (e.g., a patient's skull) to reach a target region in accordance with various embodiments. In a first step 502, characteristics of the skull are acquired using a predictive physical model and/or measurements of ultrasound transmitted and/or reflected waves from the skull. In a second step 504, multiple skull regions are defined on the skull and each skull region is characterized as an HTA region or an LTA region based on the acquired skull characteristics and an angle of incidence of the ultrasound wave with respect to the skull region. In a third step 506, ultrasound waves are transmitted to the target region and microbubbles generated or accumulated in an HTA skull region are monitored. If the amount of microbubbles is above a pre-determined threshold, a microbubble-reducing process as described above is applied to the HTA region (step 508). If the amount (number or concentration) of microbubbles is below the threshold, treatment to the target region begins or continues (step 510). Steps 506, 508 are repeated until the amount of microbubbles in the HTA skull region is below the threshold. In addition, steps 506, 508 may be applied to more than one HTA skull region. Accordingly, this approach allows the number of microbubbles generated and/or accumulated in the HTA skull region(s) to be reduced so as to increase efficiency of ultrasound treatment and avoid unexpected tissue damage resulting from microbubble cavitation.

In general, functionality for performing minimization of microbubble interferences, including, acquiring characteristics of a patient's skull (using a predictive physical model and/or measurements of ultrasound transmission and/or reflections from the skull), defining the skull as multiple skull regions, characterizing each skull region as an HTA or an LTA, monitoring microbubbles in the HTA(s), performing microbubble-reducing process, and/or starting or resuming ultrasound treatment, as described above, whether integrated within a controller of the imager, and/or an ultrasound system, or provided by a separate external controller, may be structured in one or more modules implemented in hardware, software, or a combination of both. For embodiments in which the functions are provided as one or more software programs, the programs may be written in any of a number of high level languages such as FORTRAN, PASCAL, JAVA, C, C++, C #, BASIC, various scripting languages, and/or HTML. Additionally, the software can be implemented in an assembly language directed to the microprocessor resident on a target computer (e.g., the controller); for example, the software may be implemented in Intel 80×86 assembly language if it is configured to run on an IBM PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

In addition, the term "controller" used herein broadly includes all necessary hardware components and/or software modules utilized to perform any functionality as described above; the controller may include multiple hardware components and/or software modules and the functionality can be spread among different components and/or modules.

Certain embodiments of the present invention are described above. It is, however, expressly noted that the present invention is not limited to those embodiments; rather, additions and modifications to what is expressly described herein are also included within the scope of the invention.

What is claimed is:

1. A method of reducing microbubble interference with ultrasound waves transmitted from a plurality of transducer elements and traversing a patient's skull into a target region, spaced apart from the patient's skull, in accordance with a treatment plan, the method comprising:
   (a) identifying high-throughput areas of the patient's skull through which, during execution of the treatment plan, ultrasound energy above a first threshold amount will pass;
   (b) monitoring the high-throughput areas for microbubbles during execution of the treatment plan; and
   (c) if an amount of microbubbles in the high-throughput areas exceeds a threshold, reducing the amount of microbubbles using the ultrasound waves.

2. The method of claim 1, wherein step (c) comprises generating a focus having an acoustic radiation force and using the acoustic radiation force to sweep the microbubbles outside the high-throughput areas.

3. The method of claim 2, wherein the focus is a point focus or a line focus.

4. The method of claim 1, wherein step (c) comprises generating a focus having an acoustic radiation force and using the acoustic radiation force to sweep the microbubbles from the high-throughput areas to low-throughput areas of the patient's skull, wherein ultrasound energy above a second threshold amount will not pass through the low-throughput areas during execution of the treatment plan.

5. The method of claim 4, wherein the second threshold amount is smaller than the first threshold amount.

6. The method of claim 1, wherein step (c) comprises generating a focus having an acoustic radiation force and using the acoustic radiation force to sweep the microbubbles from the high-throughput areas to intermediate-throughput areas of the patient's skull, wherein ultrasound energy above the first threshold amount will not pass through the intermediate-throughput areas but ultrasound energy above a second threshold amount, smaller than the first threshold amount, will pass therethrough.

7. The method of claim 1, wherein step (c) comprises generating an ultrasound steering beam, the ultrasound steering beam applying stress on the microbubbles to induce collapse thereof.

8. The method of claim 7, wherein the ultrasound steering beam is generated by physically moving the transducer elements with respect to the microbubbles.

9. The method of claim 7, wherein the ultrasound steering beam is generated by adjusting relative phases of the transducer elements.

10. The method of claim 1, wherein the high-throughput areas are identified based at least in part on a physical model.

11. The method of claim 1, wherein the high-throughput areas are identified based on a measurement of transmitted or reflected ultrasound waves.

12. The method of claim 1, wherein the high-throughput areas are identified based on images acquired using an imaging device.

13. The method of claim 1, wherein the high-throughput areas are identified based at least in part on an angle of incidence of the ultrasound waves with respect to the patient's skull.

14. The method of claim 13, wherein the angle of incidence is computed based at least in part on geometry of the transducer elements and their locations and orientations relative to the patient's skull and a location of the target region.

15. The method of claim 1, wherein the microbubbles are monitored based at least in part on analysis of images acquired by an imaging device.

16. The method of claim 1, wherein the microbubbles are monitored based at least in part on ultrasound waves reflected therefrom.

17. The method of claim 1, wherein each one of the high-throughput areas corresponds to one of the plurality of the transducer elements.

18. The method of claim 1, wherein each one of the high-throughput areas corresponds to one grouping of the transducer elements.

19. The method of claim 1, wherein the amount of microbubbles is defined as an absolute number thereof or as a concentration per unit volume.

20. An ultrasound treatment system comprising:
    an ultrasound transducer comprising a plurality of transducer elements; and
    a controller configured to:
    (a) operate the transducer in accordance with a treatment plan to focus ultrasound waves onto a target tissue within a patient's skull, the target tissue being spaced apart from the patient's skull;
    (b) identify, based at least on the treatment plan and an orientation of the transducer with respect to the patient's skull, high-throughput areas of the patient's skull through which, during execution of the treatment plan, ultrasound energy above a first threshold amount will pass;
    (c) monitor the high-throughput areas for microbubbles during execution of the treatment plan; and
    (d) if an amount of microbubbles in the high-throughput areas exceeds a threshold, reduce the amount of microbubbles using the ultrasound waves.

21. The system of claim 20, further comprising a detector device, coupled to the controller, for measuring the amount of the microbubbles.

22. The system of claim 20, further comprising an imager, coupled to the controller, for measuring the amount of the microbubbles.

23. The system of claim 20, wherein the controller is further configured to operate the transducer to generate a focus having an acoustic radiation force and to use the acoustic radiation force to sweep the microbubbles outside the high-throughput areas.

24. The system of claim 23, wherein the focus is a point focus or a line focus.

25. The system of claim 20, wherein the controller is further configured to operate the transducer to generate a focus having an acoustic radiation force and to use the acoustic radiation force to sweep the microbubbles from the high-throughput areas to low-throughput areas of the patient's skull, wherein through the low-throughput areas, ultrasound energy above a second threshold amount will not pass during execution of the treatment plan.

26. The system of claim 25, wherein the second threshold amount is smaller than the first threshold amount.

27. The system of claim 26, wherein the controller is further configured to operate the transducer to generate a focus having an acoustic radiation force and to use the acoustic radiation force to sweep the microbubbles from the high-throughput areas to intermediate-throughput areas of the patient's skull, wherein ultrasound energy above the first threshold amount will not pass through the intermediate-throughput areas but ultrasound energy above a second threshold amount, smaller than the first threshold amount, will pass therethrough.

28. The system of claim 20, wherein the controller is further configured to generate an ultrasound steering beam, the ultrasound steering beam applying stress on the microbubbles to induce collapse thereof.

29. The system of claim 28, wherein the controller is further configured to physically move the transducer elements with respect to the microbubbles so as to generate the ultrasound steering beam.

30. The system of claim 28, wherein the controller is further configured to adjust relative phases of the transducer elements so as to generate the ultrasound steering beam.

31. The system of claim 20, wherein the controller is further configured to identify the high-throughput areas based at least in part on a physical model.

32. The system of claim 20, further comprising a detector device, coupled to the controller, for measuring the focus ultrasound waves or ultrasound waves reflected from the patient's skull, wherein the controller is further configured to identify the high-throughput areas based on the measured focus ultrasound waves or ultrasound waves reflected from the patient's skull.

33. The system of claim 20, further comprising an imager, coupled to the controller, for acquiring images, wherein the controller is further configured to identify the high-throughput areas based on the images.

34. The system of claim 20, wherein the controller is further configured to compute an angle of incidence of the ultrasound waves with respect to the patient's skull based at least in part on geometry of the transducer elements and their locations and orientations relative to the patient's skull and a location of the target tissue.

35. The system of claim 20, wherein the controller is further configured to define the amount of microbubbles as an absolute number thereof or as a concentration per unit volume.

* * * * *